United States Patent [19]

Lewis

[11] 4,405,302
[45] Sep. 20, 1983

[54] SUPPORT FOR MOUNTING METAL MIRROR ON TEETH

[76] Inventor: Cheri J. Lewis, 240 S. La Cienega Blvd., Beverly Hills, Calif. 90211

[21] Appl. No.: 392,528

[22] Filed: Jun. 28, 1982

Related U.S. Application Data

[63] Continuation-in-part of Ser. No. 253,796, Apr. 13, 1981, Pat. No. 4,354,835.

[51] Int. Cl.³ .............................................. A61B 1/24
[52] U.S. Cl. ................................................... 433/30
[58] Field of Search ............................. 433/31, 34, 30

[56] References Cited

U.S. PATENT DOCUMENTS 939,834 11/1909 Harper ................................. 433/30

Primary Examiner—Robert Peshock
Attorney, Agent, or Firm—Dominick Nardelli

[57] ABSTRACT

The support has an elongated body whereon at one end is swivel mounted a dental mirror and at the other end is disposed a spring clip means which is capable of engaging a tooth so that the mirror is independently supported within the mouth of the person wherein dental work is being performed.

2 Claims, 4 Drawing Figures

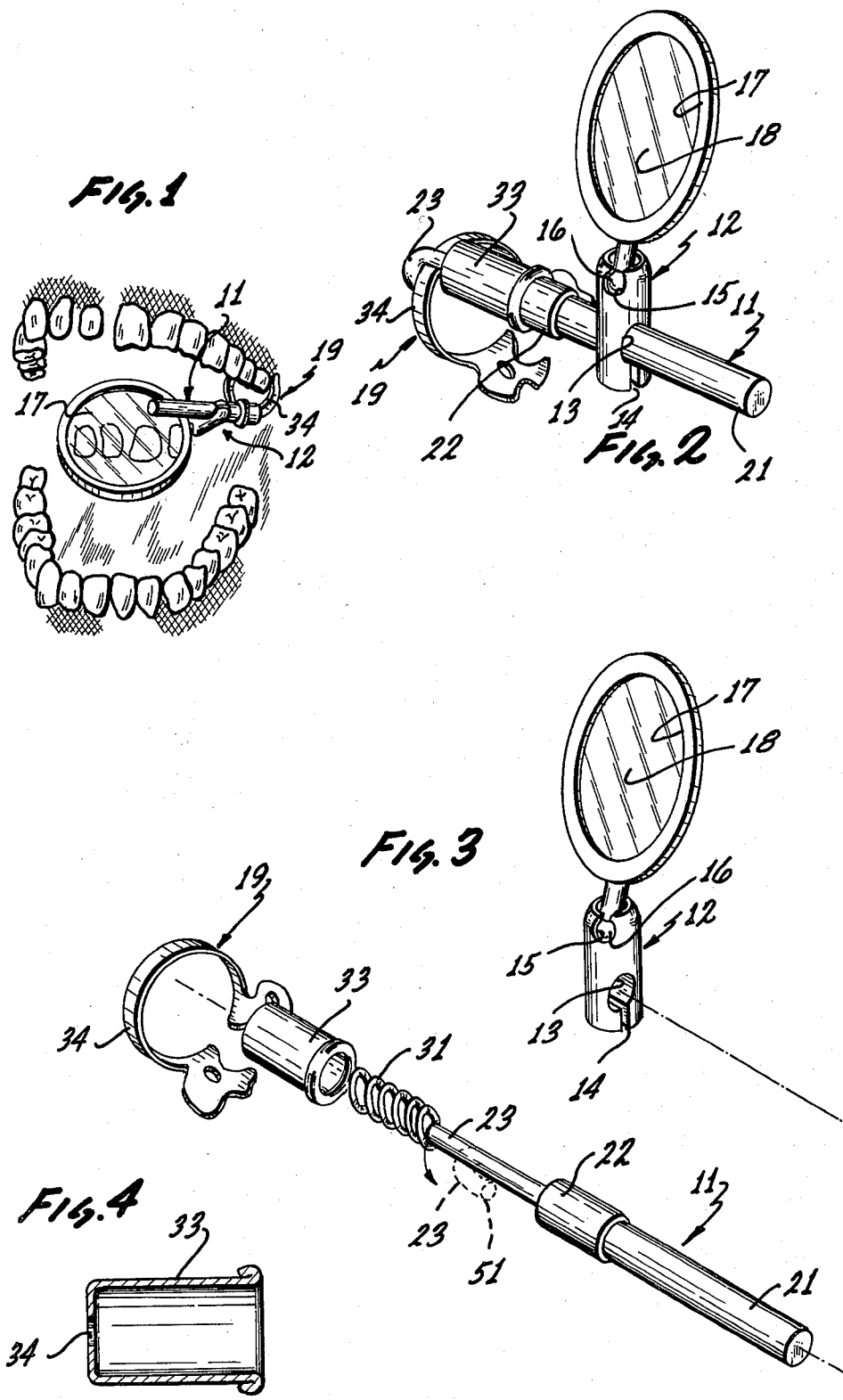

SUPPORT FOR MOUNTING METAL MIRROR ON TEETH

This application is a continuation-in-part of my copending application Ser. No. 253,796, filed Apr. 13, 1981 and now U.S. Pat. No. 4,354,835 issued Oct. 19, 1982.

FIELD OF THE INVENTION

This invention relates to dental mirrors and more particularly to dental mirrors that have a means of support which mount onto a person having dental problems.

BACKGROUND OF THE INVENTION

Almost everyone has seen dental mirrors and known something about their utility. One of the main functions of a dental mirror is to allow the dentist to view the commonly unseen sides of a persons teeth, which sides face the interior of the mouth. Up to now, dental mirrors consisted of a round spectral disk mounted at an angle at the end of a long slender rod. To use the mirror the dentist, depending on whether he was right or left handed, held a working tool, such as a drill in one hand, and the mirror in the other hand. Thus both hands were occupied, and if another tool is needed, obviously, the first tool had to be set down before the second tool could be picked up. One can see that the dentist was limited to using one tool at a time.

As the art of dentistry progressed, the dentist discovered that in some cases, he could perform a better job if he could use two working tools at the same time instead of having one hand tied to a dormant device such as the mirror, which is only an aid to the dentist in performing his duties. In such situations, some dentists summon an assistant to help them. However, this is undesirable, because to many hand would be located within the region of the mouth.

OBJECT OF THE INVENTION

An object of this invention is to provide a simple practical means for supporting a mirror as used in dentistry.

Another object of this invention is to provide a means which allows one to fixedly mount a dental mirror to one's teeth so that the mirror is disposed within the cavity of the mouth.

These and other objects and features of advantages will become more apparent after one studies the following description of the preferred improved embodiment of my invention together with the appended drawing.

BRIEF DESCRIPTION OF THE DRAWING

FIG. 1 is a schematic representation of a patient's open mouth wherein the mirror with the novel support means is placed.

FIG. 2 is an assembled pictorial view of the dental mirror with the support means, both removed from one's mouth.

FIG. 3 is an exploded practical view of the support means of FIG. 1 showing the individual parts.

FIG. 4 is an axial section of the cup part on the support means.

DETAILED DESCRIPTION OF THE DRAWING

Referring to the drawing, and to FIG. 1 in particular, the novel support means has a cylindrical body 11 onto which is slideably mounted a link 12 through its aperture 13 (FIG. 3). A slot 14 is formed at one end of link 12 and extends to aperture 13 to provide a springing action between the body 11 and the link 12 so that friction is used to hold the two items in a releaseable and fixed relationship. In most applications this slot 14 is not needed. At the other end of link 12 is formed a standard socket 15 into which is disposed a ball 16 which in turn is made integral with a disk shaped mirror 17. The spectral surface 18 of the mirror 17 is recessed below an annular rim therearound. On one end of the body 11 is disposed a standard spring clip 19 which is of standard design and is used by a dentist to grip a tooth. The length of the body 11 is such that it is capable of being disposed within a patients open mouth while clip 19 is gripping a tooth as shown in FIG. 1.

One can see that when my novel support is disposed within a patients open mouth the mirror 17 can be moved to any position and it is fixed in that position until again moved.

Referring to FIG. 3, there is shown the improved preferred embodiment of my invention unassembled. This construction allows the support to be readily disassembled to be put into an autocave or a sterilizing unit so as to insure sterilization. The spring clip 19 which is of a standard design is shown removed from the remaining parts. The body 11 is made preferably of metal such as soft aluminum. The body 11 has a cylindrical end 21 as shown, to which is attached a cylindrical midsection 22 having a larger diameter than end 21. On the other side of the midsection 22 is attached a slender cylindrical hook end 23.

Before the support is assembled, the hook end 23 is straight or cylindrical as shown by the solid lines in FIG. 3. The support is first assembled before it is completed or finished. Therefore, a compression coil spring 31 is threaded over hook end 23 and a cup 33, which has a centrally disposed aperture 34, as shown in FIG. 4 at its closed end, is then threaded onto the end 23 so that the cylindrical side wall of the cup 33 encloses the spring 31. The diameter of the aperture 34 in the cup 33 is slightly larger than the diameter of end 23 and the inside diameter of cup 33 is such that the midsection 23, when assembled freely slides therein. After the spring 31 and cup 33 are assembled and spring 31 is compressed, the extreme end of the hook end 23 is bent 180 degrees to the shape as shown by the dash lines 51 in FIG. 3 so that there is sufficient space for the bight portion 34 of clip 19 to be nested therein as shown in FIG. 2. One understands that the spring 31 within cup 33 urges the apertured end of the cup 33 against the bight portion 34 securing the two parts together. Whenever the unit needs to be sterilized one needs only to compress spring 31 by urging the side wall of cup 33 over the midsection 22 and the clip 19 is freed. As an alternative, whenever the mirror 17 is required to be located closer to the clip 19, another link 12 can be made available by one skilled in the art, wherein the diameter of its hole 13 is sufficiently large to be able to slideably engage the outer support of the cup 33.

Having described the preferred embodiment of my invention, one skilled in the art, after studying the description of my preferred embodiment, could devise other embodiments without departing from the spirit of my invention. Therefore, my invention is not limited to the disclosed embodiment, but includes all other embodiments falling within the scope of the appended claims.

I claim:

1. A support for a dental mirror capable of being mounted onto a spring clip, said support comprising:

a cylindrical body having a first cylindrical section of a first diameter and a second cylindrical section of a second diameter which is smaller than said first diameter;

a hook end disposed on said second section opposite said first section with a coil spring disposed between the hook end and against the first cylindrical section, a cup having an axially aperture and said cup is disposed between said spring and said hook, said cup being urged by the spring against the spring clip when the hook is mounted to engage the spring clip;

a link slideably mounted on said first cylindrical section;

said link having a socket formed at one end;

said mirror being and having a radially protruding ball formed thereon;

said ball being disposed within said socket in swivel relationship therein.

2. In the support of claim 1 wherein:

a midsection is disposed axially aligned to and between said first and second cylindrical sections and has a larger diameter than both said first and second sections.

* * * * *